(12) United States Patent
Yim (10) Patent No.: US 10,499,930 B2
(45) Date of Patent: Dec. 10, 2019

(54) METHOD, SYSTEM, AND APPARATUS FOR BONEY STRUCTURE TAP

(71) Applicant: TorreySpine, Inc., San Diego, CA (US)

(72) Inventor: Jason Yim, Cardiff, CA (US)

( * ) Notice: Subject to any disclaimer, the term of this patent is extended or adjusted under 35 U.S.C. 154(b) by 0 days.

(21) Appl. No.: 13/771,071

(22) Filed: Feb. 19, 2013

(65) Prior Publication Data

US 2014/0100575 A1    Apr. 10, 2014

Related U.S. Application Data

(60) Provisional application No. 61/599,931, filed on Feb. 16, 2012.

(51) Int. Cl.
*A61B 17/16* (2006.01)
*A61B 90/00* (2016.01)

(52) U.S. Cl.
CPC .... *A61B 17/1655* (2013.01); *A61B 2090/062* (2016.02)

(58) Field of Classification Search
CPC .......... A61B 17/1655; A61B 2019/462; A61B 17/8625; A61B 19/46; A61F 2/4657; F16B 25/0057
USPC ......... 606/79, 80, 96, 102, 300–321, 92–94; 411/395, 412, 413
See application file for complete search history.

(56) References Cited

U.S. PATENT DOCUMENTS

| | | | | |
|---|---|---|---|---|
| 126,366 | A * | 4/1872 | Willis ................. | F16B 25/0015 411/387.3 |
| 3,915,162 | A * | 10/1975 | Miller ........................ | 606/316 |
| 4,778,319 | A * | 10/1988 | Schule .................. | E04D 3/3603 411/387.4 |
| 6,030,162 | A * | 2/2000 | Huebner ...................... | 411/413 |
| 2003/0018337 | A1 * | 1/2003 | Davis ............................ | 606/80 |
| 2005/0101961 | A1 * | 5/2005 | Huebner et al. ................ | 606/72 |
| 2005/0107800 | A1 * | 5/2005 | Frankel et al. ................ | 606/92 |

* cited by examiner

*Primary Examiner* — Si Ming Ku
(74) *Attorney, Agent, or Firm* — Merle W Richman, III (57) ABSTRACT

Embodiments of a bony structure tap with a plurality of landmarks. Other embodiments may be described and claimed.

18 Claims, 10 Drawing Sheets

FIGURE 2E

METHOD, SYSTEM, AND APPARATUS FOR BONEY STRUCTURE TAP

CROSS REFERENCE TO RELATED APPLICATIONS

This application is related to U.S. Provisional Application No. 61/599,931, filed Feb. 16, 2012, entitled "METHOD, SYSTEM, AND APPARATUS FOR BONEY STRUCTURE TAP", and assigned Attorney Docket No. TS002US, which is incorporated by reference herein.

TECHNICAL FIELD

Various embodiments described herein relate generally to tapping or creating an opening for a threaded implant in a bony structure, including systems and methods for creating an opening for a threaded implant in a bony structure.

BACKGROUND INFORMATION

It may be desirable to creating an opening for a threaded implant in a bony structure in a closed, semi-closed, or occluded field and monitor the depth of the opening or tapping.

DETAILED DESCRIPTION

Figure 1A:
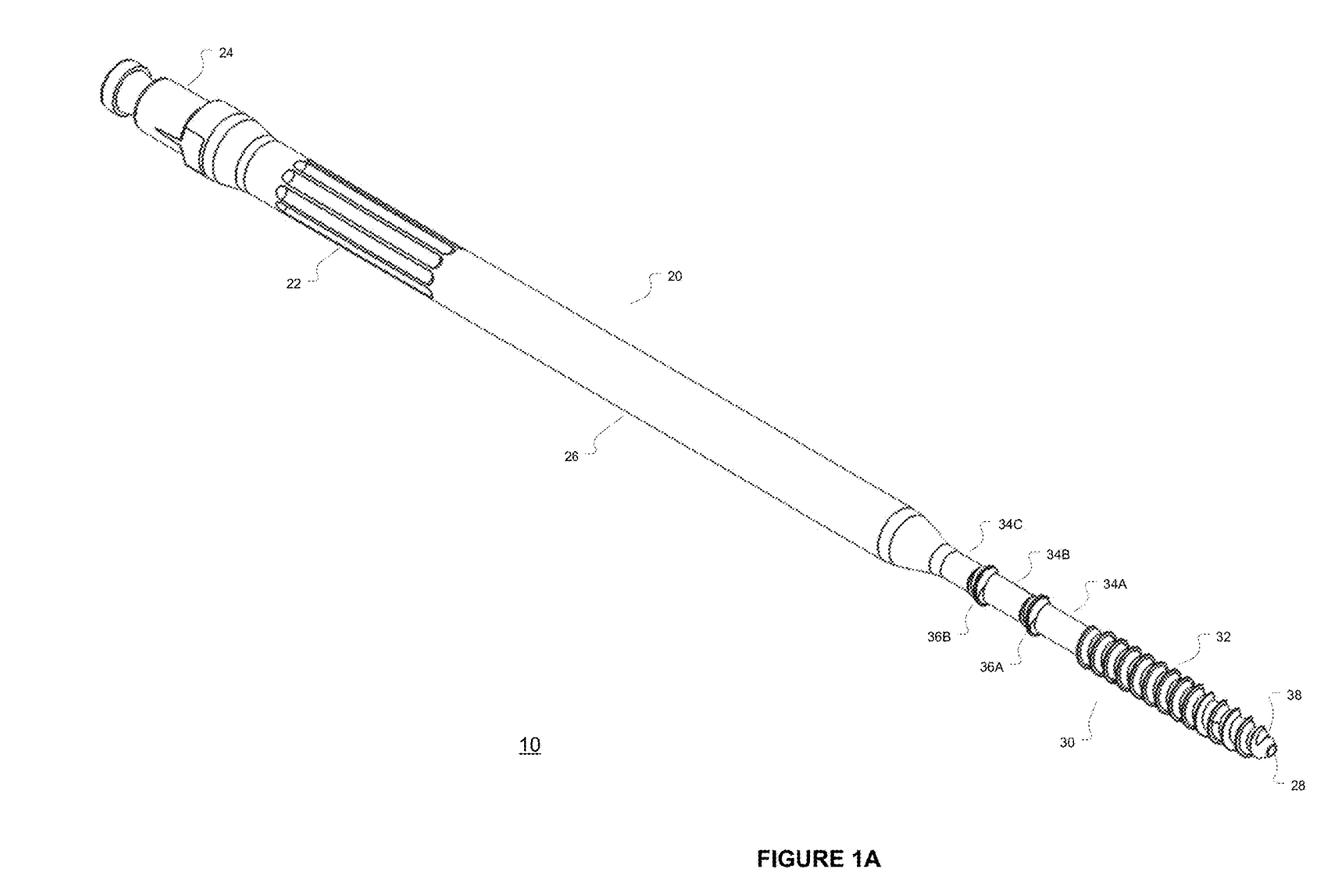
FIG. 1A is an isometric diagram of a mammalian bony segment tap system according to various embodiments.

FIG. 1A is an isometric diagram of a mammalian bony segment tap system 10 according to various embodiments. The bony segment tap system (BSTS) 10 may include a distal tapping section 30 and handle 20. The handle 20 may include a proximal tool coupling interface 24, extension 26, and grip 22 therebetween. In an embodiment a tool such as a fixed or ratcheting tool may be removably coupled to the tool coupling interface 24. In another embodiment a fixed or ratcheting tool may be fixably coupled to the tool coupling interface 24 or directly to the handle section 20.

The distal tapping section 30 may include a distal tap section 32 and one or more depth markers 36A to 36B. In an embodiment a depth marker 36A may be separated from the distal tap section 32 by a smooth, smaller diameter section 34A. In addition a second smaller diameter may separate the first depth marker section 36A from the second depth marker 36B. A further smaller diameter section 34C may separate the second depth marker 36B from a larger diameter extension 26 of the handle 20. In an embodiment the first and the second depth markers or depth marking sections 36A, 36B may be small tap sections that are spirally aligned with the tap section 32 (as shown in FIG. 1G if the tap section 32 spiral threads were extended to depth marking section 36A, the spirals would coincide or link radially about the longitudinal axis of the tap system 10 (the longitudinal axis extending from the tool interface 24 to the distal, slanted end 38.)

In an embodiment the entire BSTS 10 may be cannulated 28 along the longitudinal axis so the BSTS 10 may be inserted over a K-wire or guide-wire 60 (FIG. 2A) in an embodiment. In an embodiment the cannulation 28 may have a radius of 1 to 2 mm or about 1.5 mm. It is noted the BSTS 10 may have an overall length of about 140 mm to 300 mm or about 220 mm in an embodiment. The maximum radius of the tap section 32 threads 39E (FIG. 1F) may vary as a function of the radius the respective threaded implant (50A to 50D, FIGS. 4A to 4D). In an embodiment a threaded implant maximum thread radius 39E of the tap section 32 may be smaller than the respective threaded implant 50A 50D outer radius (of its threads 54A to 54D) to provide a secure coupling between the tapped bony section 222B (FIG. 2E) and the threaded implant 50. In an embodiment the BSTS 10 maximum thread diameter 39E may be about 4.0 mm, 5.0 mm, 6.0 mm, and 7.0 mm where the corresponding threaded implant 50 thread 54A to 54D outer diameter is about 4.5 mm, 5.5 mm, 6.5 mm, and 7.5 mm, respectively.

The BSTS 10 distal tap section 32 length may vary as a function of the tap depth needed in a bony structure. Similarly the one or more partial thread depth markers 36A, 36B distance from the BSTS 10 tip 38 may vary of a function of possible tap depths for a bony structure and the possible lengths of the threaded implant 50A to 50D threaded sections 54A to 54D. In an embodiment a threaded implant 50A to 50D threaded sections 54A to 54D may have a length from about 30 mm to 70 mm. In an embodiment the threaded sections 54A to 54D may have predetermined different lengths to accommodate different bony structure and patient structures such as 35 mm, 40 mm, 45 mm, 50 mm, 55 mm, and 60 mm.

The distance between spirals 39A, 39B, 39C, 39D, and 39E may be fixed and may be a function of the corresponding threaded implant 50A to 50D, 50 to be implanted into the tap or opening formed by the use or operation of the BSTS 10. Similarly the height or peak, leading edge angle, and trailing edge angle of the threads 39A to 39E, 36A, 36B may be a function of the corresponding threaded implant 50A to 50D, 50 to be implanted into the tap or opening formed by the use or operation of the BSTS 10. In an embodiment the width between adjacent threads, spirals, peaks 39A to 39E, 36A, 36B may be about 1.5 to 3.0 mm and about 1.9 mm or 2.5 mm in an embodiment. The leading edge angle of threads, spirals, peaks 39A to 39E, 36A, 36B may be about 20 to 30 degrees or about 24 degrees in an embodiment. The trailing edge angle threads, spirals, peaks 39A to 39E, 36A, 36B may be about 7 to 20 degrees or about 12 degrees in an embodiment.

Figure 1B:
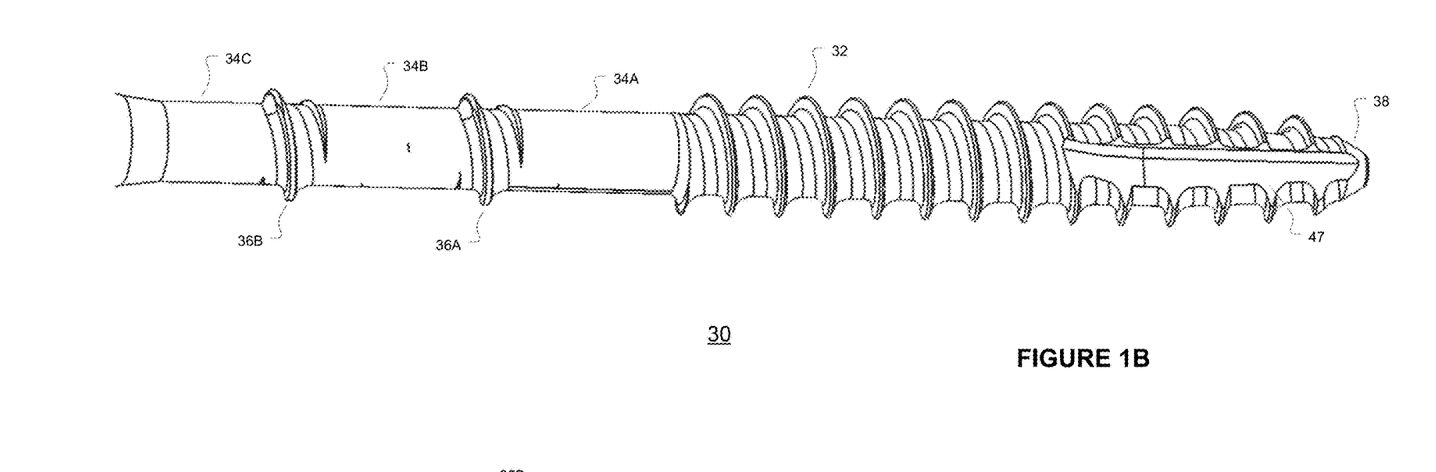
FIG. 1B is a diagram of a mammalian bony segment tap system distal tapping section according to various embodiments.

FIG. 1B is a diagram of a mammalian bony segment tap system distal tapping section 30 according to various embodiments. As shown in FIG. 1B the distal section 32 may include a plurality of threads or spirals that increase in diameter from the tip 38. In an embodiment the tip 38 also be beveled and include a cut out 47 to ease introduction and rotation into a bony structure. In an embodiment the bevel may have about a 60 degree relative to the longitudinal axis. As also shown in FIG. 1B, each partial spiral depth marker section 36A, 36B may be separated from adjacent spirals and extension 26 by a section 34A, 34B, and 34C. In an embodiment the sections 34A, 34B, 34C may have a uniform length. Further the distance from last spiral in section 32 to peak spiral 36A from peak spiral 36A to peak spiral 36B may also have a uniform or known distance. In an embodiment the spiral 32 length is also known. Accordingly, the distance from the tip 38 to the last spiral of section 32, the spiral 36A, and the spiral 36B may be known.

During a tapping procedure the location of these landmarks relative to the bony structure may enable a user to determine the depth of the tap formed via the BSTS 10 (such as shown in FIGS. 2A to 2D). In particular in a closed procedure or occluded field radiographic images (such as simplified images shown in FIGS. 3A to 3D) may also show these landmarks (each of 32, 36A, 36B) relative to the bony structure and may enable a user to determine the depth of the tap or threads formed via the BSTS 10. In an embodiment the BSTS 10 or at least the distal section 30 may be formed of a radio-opaque material including a metal, alloy or treated ceramic. In an embodiment the BSTS 10 may be formed of a stainless steel material including SUS631 with a HRC of 45. In an embodiment the landmarks (end of section 32, position of 36A, and position of 36B may be based on common lengths of threaded implants 50A to 50D threaded sections 54A to 54D to be inserted into a bony structure 222B. As noted above threaded sections 54A to 54D may have predetermined different lengths of about 35 mm, 40 mm, 45 mm, 50 mm, 55 mm, and 60 mm. In an embodiment the end of section 32 may be about 35 mm (from the tip 38), location of 36A may be about 45 mm from the tip 38, and the location of 36B may be about 55 mm from the tip 38.

Figures 2A, 3A:
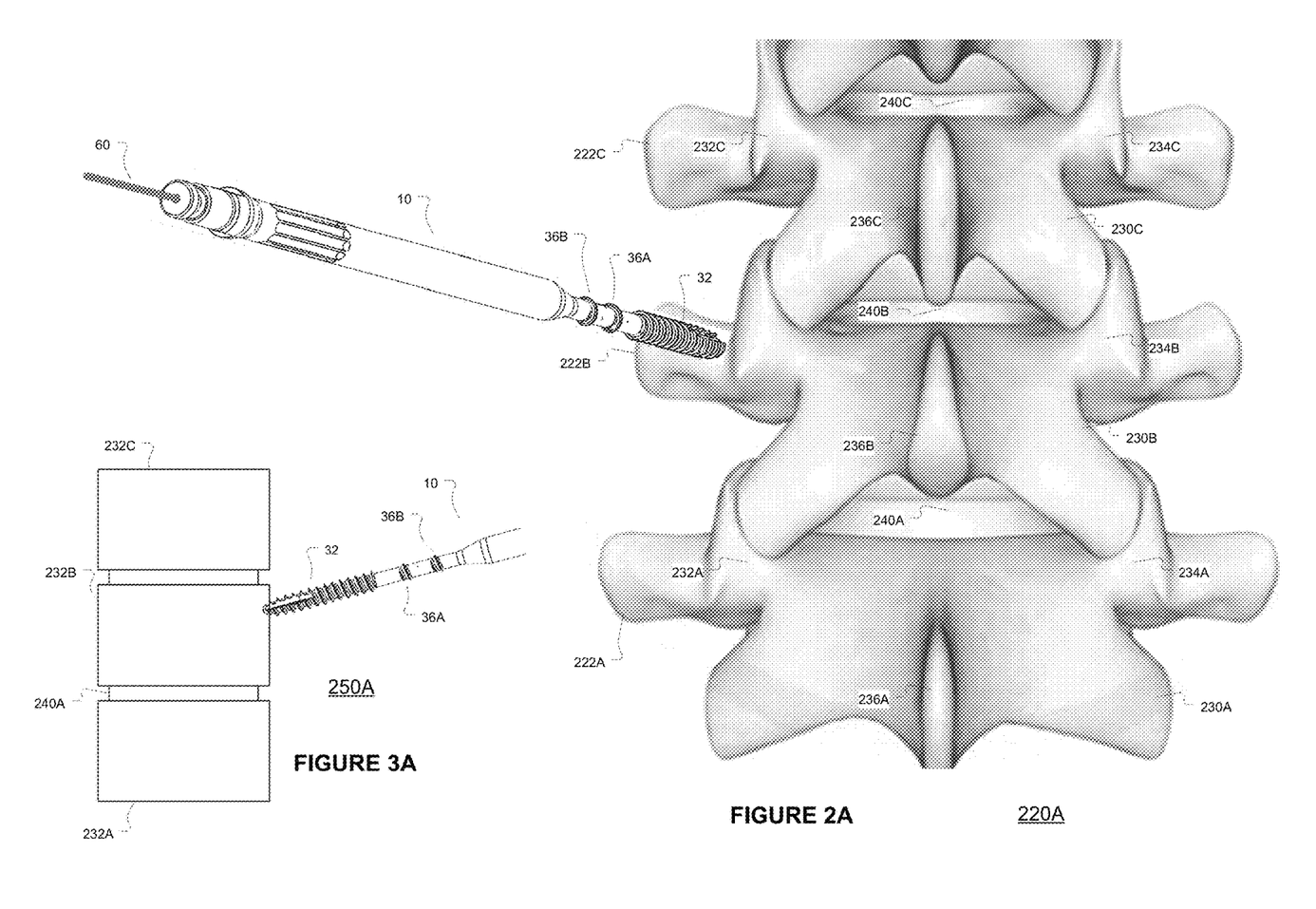
FIGS. 2A to 2D are simplified posterior diagrams of a mammalian bony segment tap system processing a mammalian bony segment according to various embodiments.
FIG. 3A to 3D are simplified side, sectional diagrams of a mammalian bony segment tap system processing a mammalian bony segment according to various embodiments.
Figure 4:
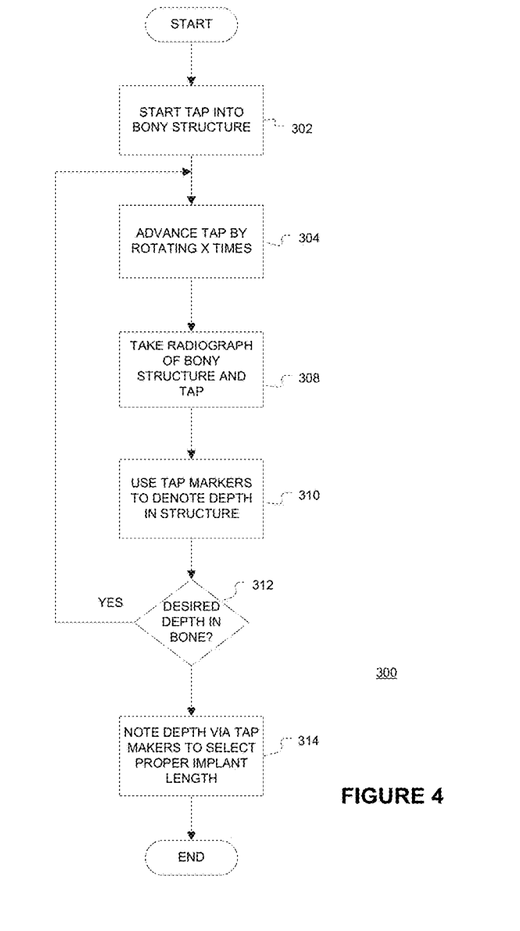
FIG. 4 is a flow diagram illustrating mammalian bony segment stabilization algorithms according to various embodiments.

Based on these know landmark locations a user (such as a physician or physician assistant, or veterinarian may employ the BSTS 10 to tap a bony structure and simultaneously determine the implant size appropriate for the bony structure and formed opening. In an embodiment a practitioner may employ the process shown in FIG. 4 in conjunction with the BSTS 10 to form a tapped opening in a bony structure. As shown in FIG. 2A, 220A a practitioner may start the BSTS 10 into a bony structure 222B activity 302. FIG. 3A shows a side image 250A of the BSTS 10 starting a tapped or threaded opening in a bony structure where the image or diagram 250A may be generated by a radiographic device such as a C-arm.

Figures 2B, 3B:
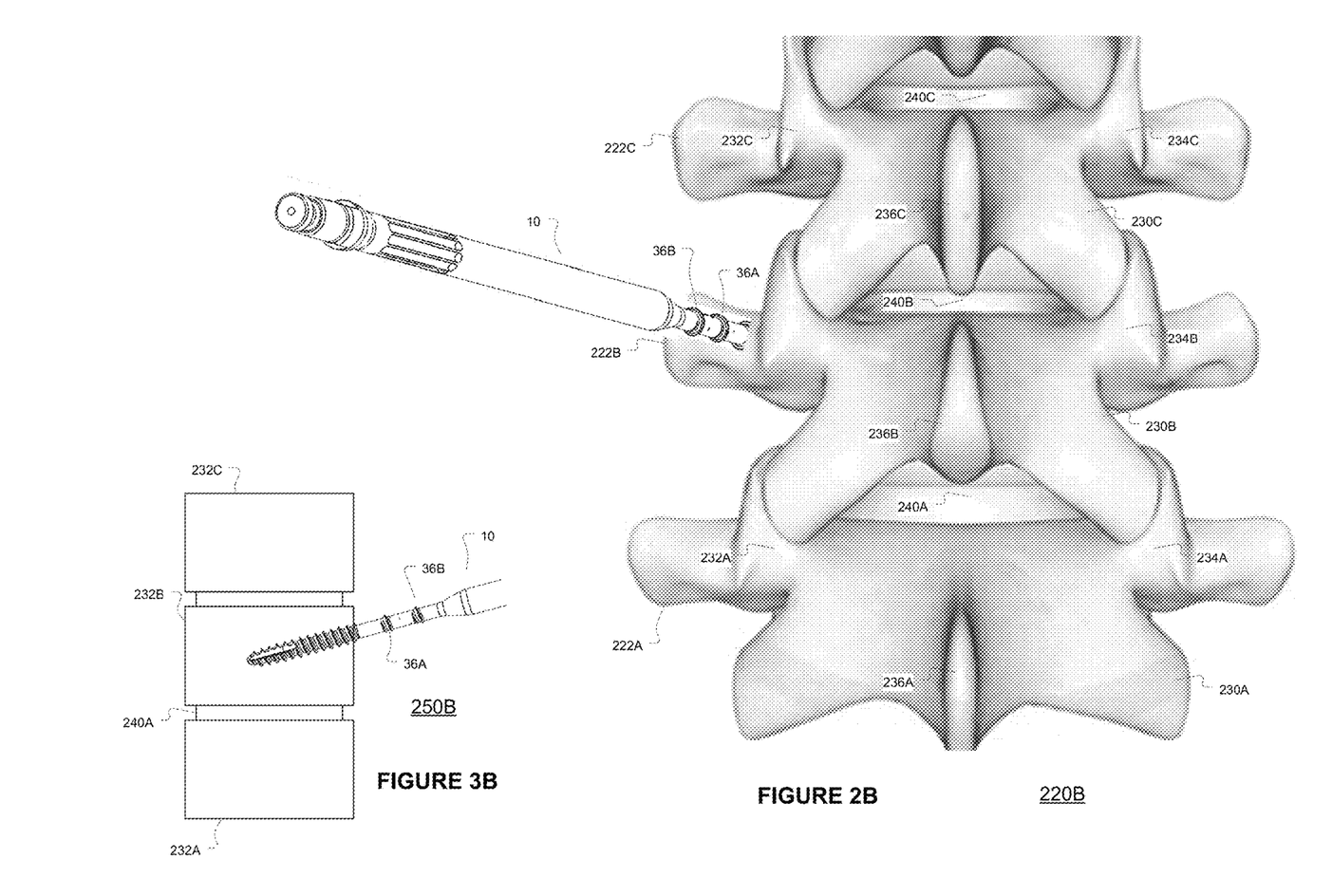
Figures 2C, 3C:
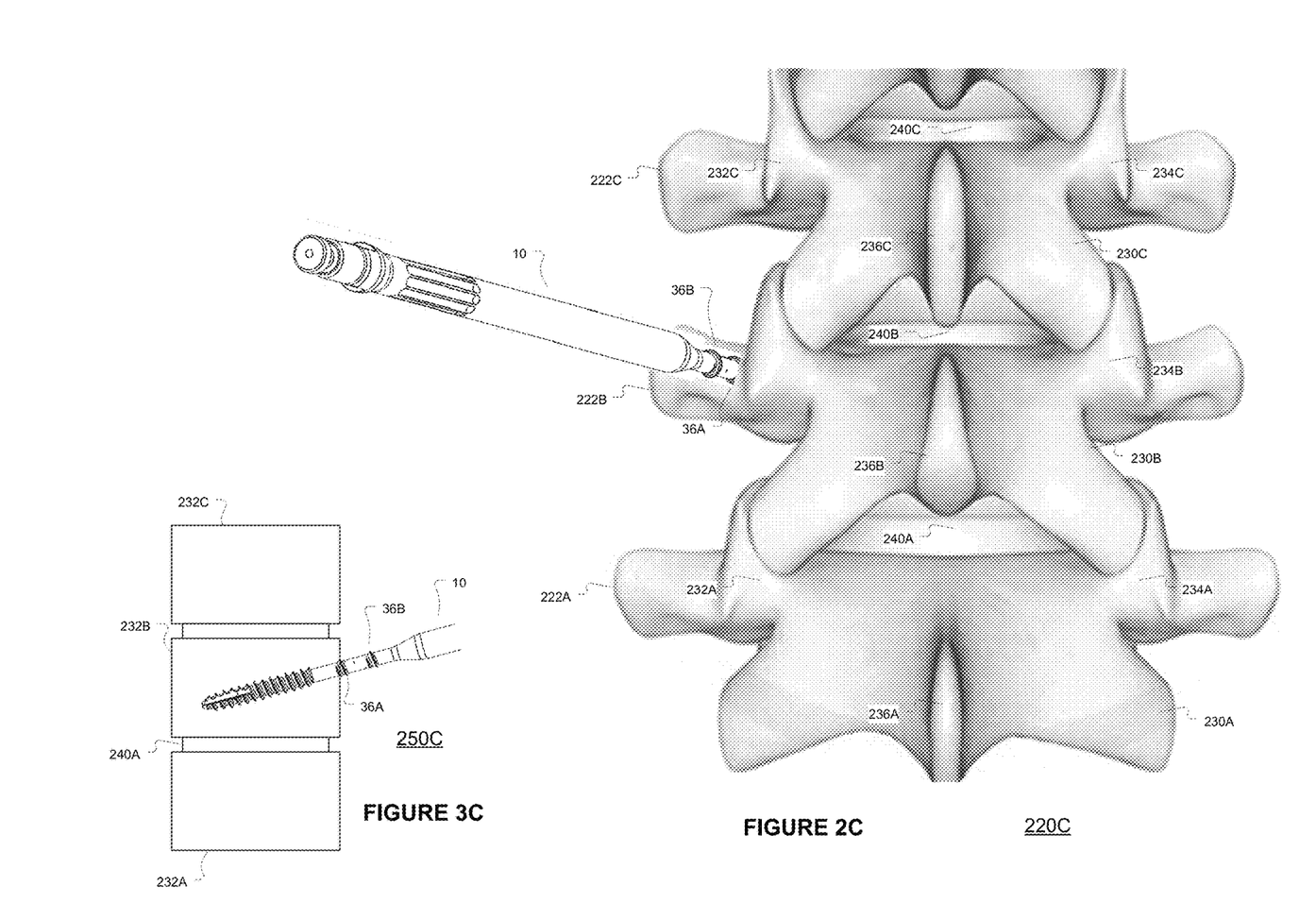
Figures 2D, 3D:
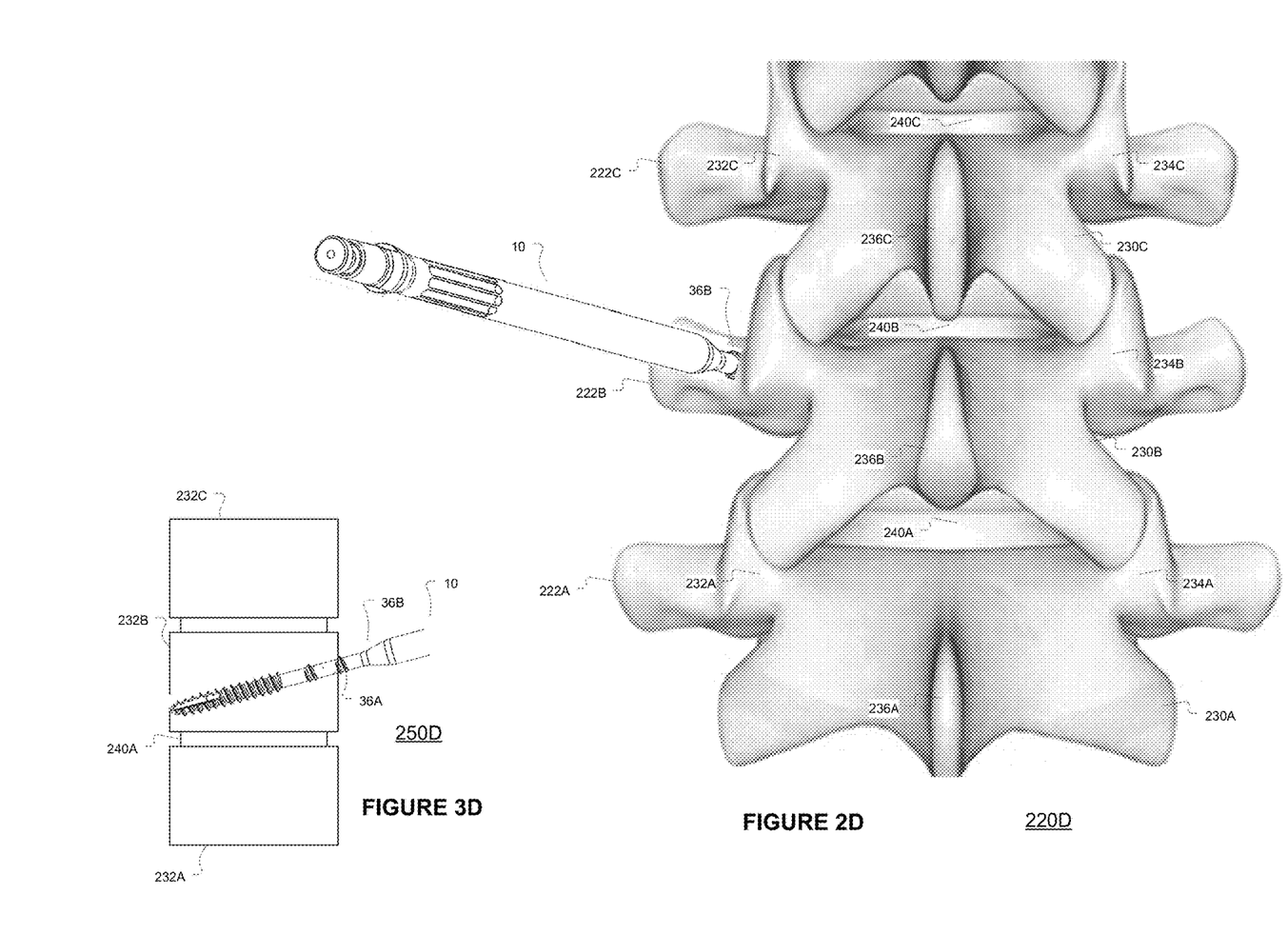

As shown in FIG. 2B, 220B a practitioner may continue to form the tapped opening into a bony structure 222B via the BSTS 222B by rotating the BSTS 10 a predetermined number of complete rotations activity 304. A practitioner may then take a radiographic image (activity 308) and use the landmarks 32, 36A, 36B to determine the depth of the tap and location of tap tip 238 relative to bony structure boundaries (activity 310). FIG. 3B shows a side image 250B of the BSTS 10 with a tapped or threaded opening in a bony structure up to the end of the tap section 32 where the image or diagram 250B may be generated by a radiographic device such as a C-arm.

If the desired depth is achieved (activity 312) then a practitioner may use the landmarks 32, 36A, 36B to select a proper length implant 50A to 50D threaded section 54A to 54D for implantation into the formed threaded opening (activity 314). Otherwise a practitioner may repeat activities. For example a practitioner may advance the tap to the landmark 36A (shown in FIG. 2C, 220C, FIG. 3C, 250C) or landmark 36B (shown in FIG. 2D, 220D, FIG. 3D, 250D) if the bony structure boundaries support such depths.

Figure 1C:
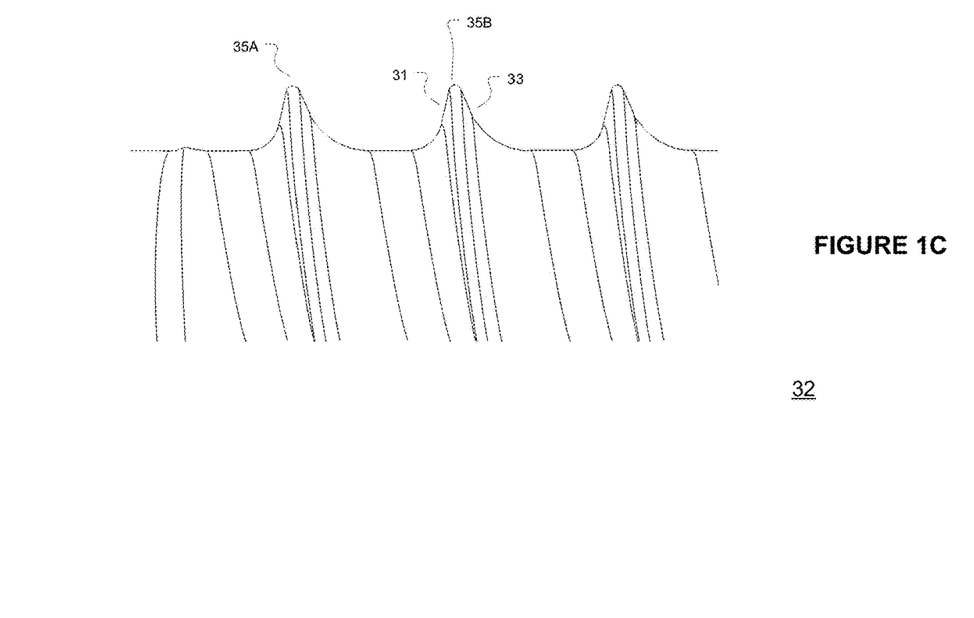
FIG. 1C is a diagram of a mammalian bony segment tap system distal tapping, thread section according to various embodiments.
Figure 1D:
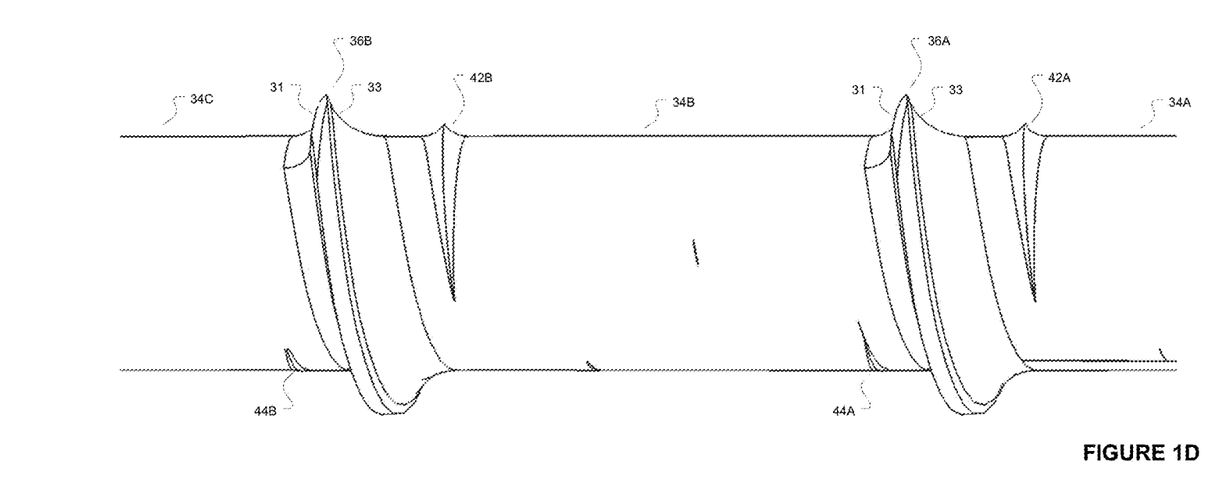
FIG. 1D is a diagram of a mammalian bony segment tap system distal depth markers according to various embodiments.
Figure 1E:
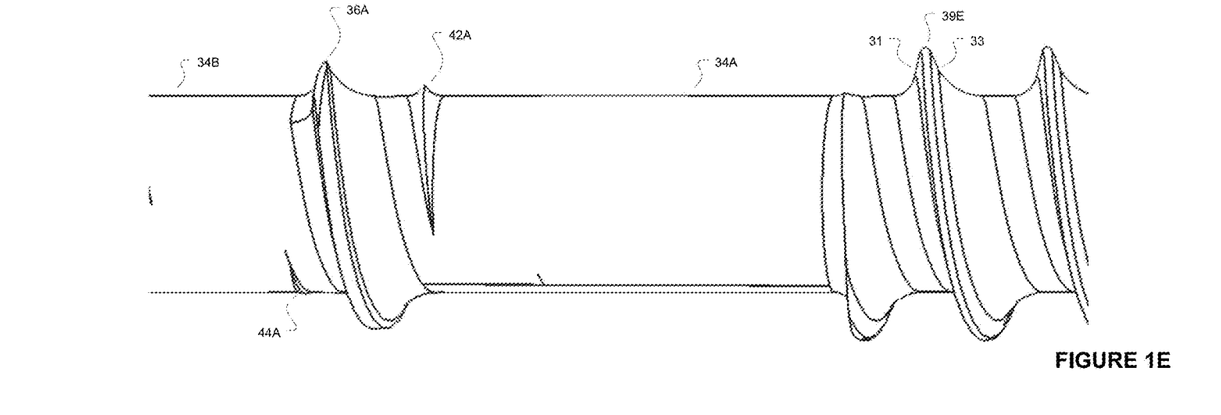
FIG. 1E is a diagram of a mammalian bony segment tap system distal depth marker and thread section according to various embodiments.

Then a practitioner may insert an implant 52 with a threaded section 54C having a desired or selected length based on the BSTS 10 noted landmarks 32, 36A, 36B. As noted and shown in FIG. 1G, the landmarks 36A, 36B are partial spirals that would correspond with the spiral pattern formed by the distal section 32 if the distal section 30 spiral 32 was extended (45A, 45B, 45C, 45D). This configuration helps guide the BSTS 10 sections 36A, 36B into the threads formed in the bony structure by the distal section 30 spirals or threads 32. As noted above and shown in FIG. 1C the distance between two adjacent threads 35A, 35B (of a spiral 32) and the forward pitch 33 and reverse or back pitch 31 may be selected as a function of the implant thread section 54A to 54D to be inserted into the formed, threaded, opening in a bony structure 222B. FIG. 1D shown that the landmarks 36A, 36B spirals have the same forward and reverse pitch 33, 31 as the spiral 32 and have a section 34B without spirals 34B between the landmarks 36A, 36B and more proximal section 34C after the landmark 36B without spirals. FIG. 1E shows that another section 34A between the spiral 32 and landmark 36A may also not include spirals. In an embodiment the sections 34A and 34B may be about the same length.

Figure 1F:
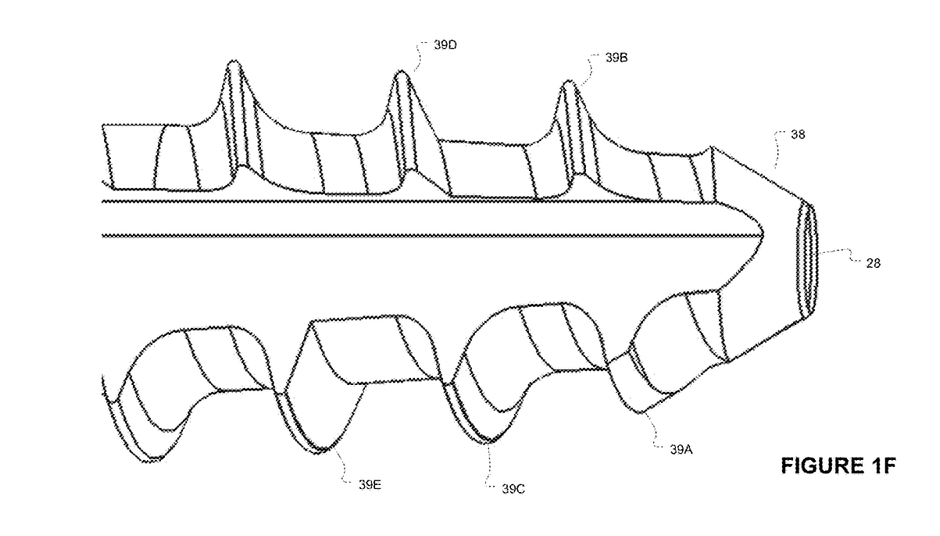
FIG. 1F is a diagram of a mammalian bony segment tap system distal tapping, thread section tip according to various embodiments.
Figure 1G:
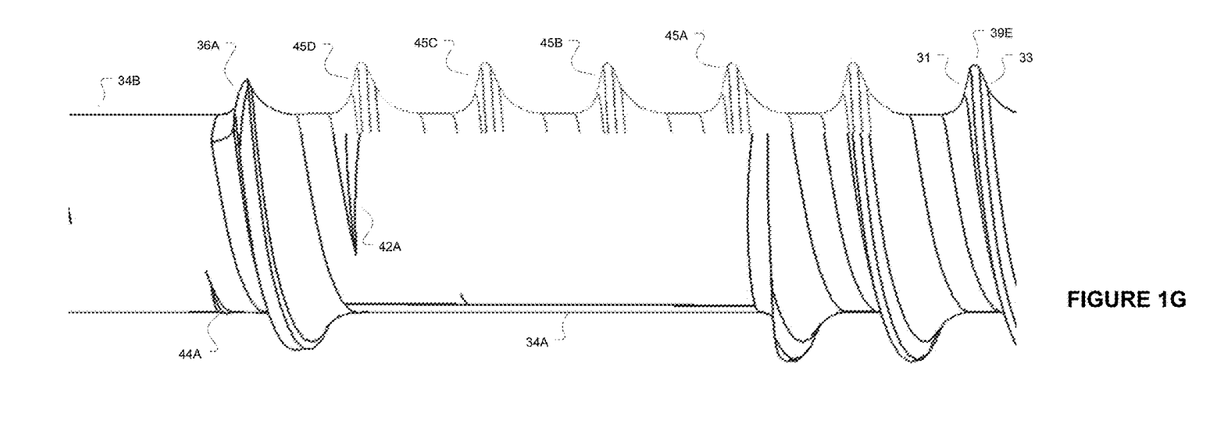
FIG. 1G is a diagram of a mammalian bony segment tap system distal depth marker and thread section with representative cut threads or taps linking same according to various embodiments.
Figures 2E, 3E, 4A, 4B, 4C, 4D:
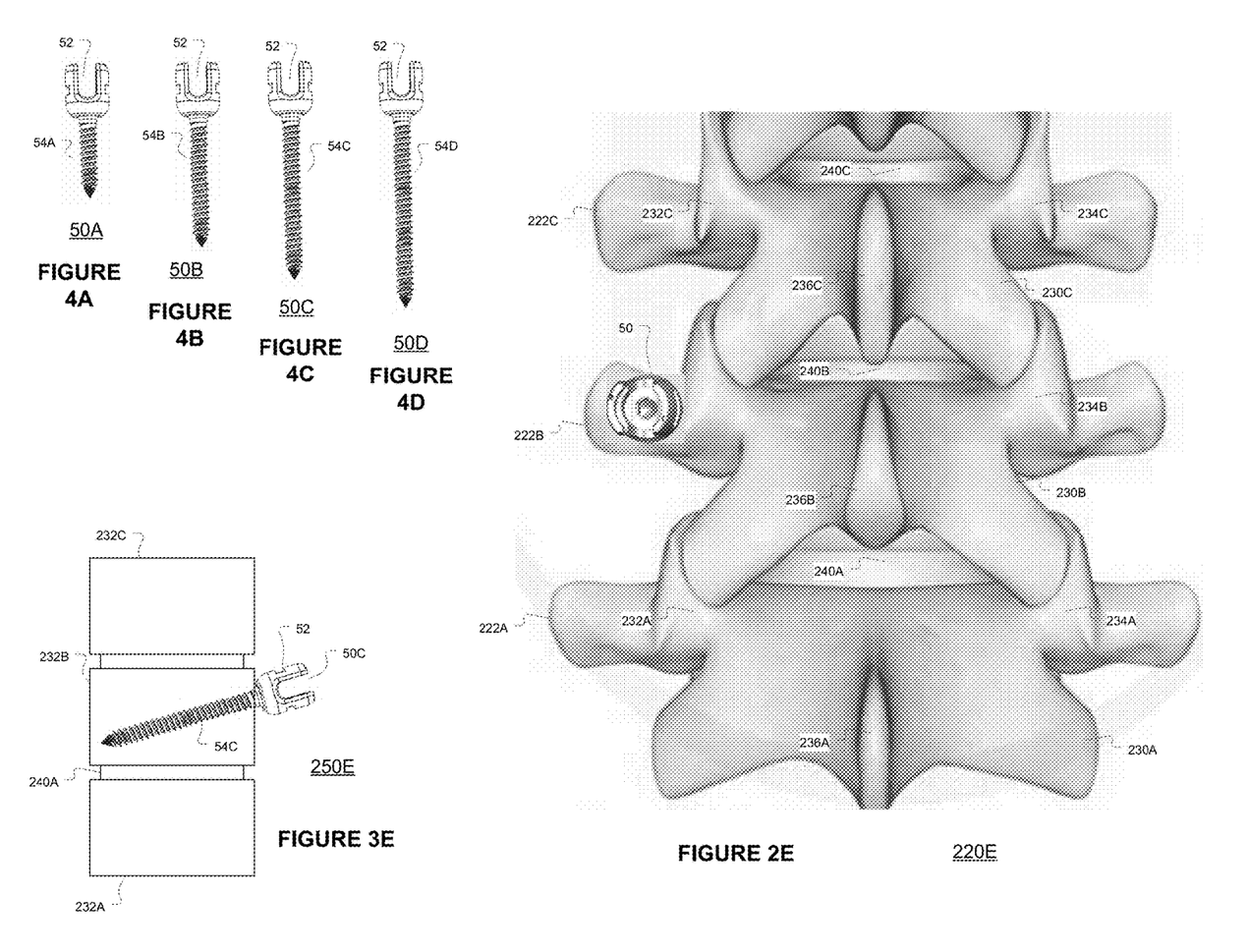
FIG. 2E is a simplified posterior diagrams of a mammalian bony segment implant coupled to a mammalian bony segment according to various embodiments.
FIG. 3E is a simplified side, sectional diagram of a mammalian bony segment implant coupled to a mammalian bony segment according to various embodiments.
FIG. 4A to 4D are simplified front diagrams of a mammalian bony segment threaded implants according to various embodiments.

FIG. 1F shows the distal spiral 32 threads 39A, 39B, 39C, 39E may increase from a minimal diameter to a maximum diameter where the difference between the minimal diameter 39A and maximum diameter for a thread 39E may be about 1 mm (or about 0.6 mm in an embodiment). In an embodiment the BSTS 10 may be employed to create a threaded opening in a spinal vertebra 222A, 222B, 222C pedicle process 232C, 234C, 232B, 234B, 232A, 234A where a disc 240A, 240B, 240C may separate adjacent vertebra 222A, 222B, 222C and the vertebra 222A, 222B, 222C may include dorsal processes 236A, 236B, 236C. The implants 50, 50A to 50D with threaded sections 54A to 54D may be poly-axial or mono-axial pedicle screws. The screws may also be cannulated so the screws 50, 50A, 50D may be inserted over the guide wire or K-wire 60 after the BSTS 10 has been removed from the bony structure.

Further the bony regions 222A, 222B, 222C may be vertebra separated by spinal discs 240A, 240B, 240C in a cervical, thoracic, or lumbar region of a mammal including a human. In embodiment each bony segment 222A-C may include a pedicle pair 232A-C, 234A-C, and a dorsal spinous process 236A-C.

The accompanying drawings that form a part hereof show, by way of illustration and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In the foregoing Detailed Description, various features are grouped together in a single embodiment for the purpose of streamlining the disclosure. This method of disclosure is not to be interpreted to require more features than are expressly recited in each claim. Rather, inventive subject matter may be found in less than all features of a single disclosed embodiment. Thus the following claims are hereby incorporated into the Detailed Description, with each claim standing on its own as a separate embodiment.

What is claimed is:

1. A dense tissue tap apparatus for creating a threaded tap of a first diameter within a dense tissue to a known depth, comprising:
    an elongated shift including a proximal end, a distal end, and a longitudinal axis between the ends, the shaft including a non-tapping section at the proximal end and a tapping section at the distal end, the tapping section including:
        a continuous tapping section extending from a distal most end and having a first length and including a tapping thread having a first maximum outer diameter that may create a threaded tap of the first diameter in dense tissue; and
        a first reduced diameter section immediately and proximately adjacent the continuous tapping section, the first reduced diameter section having a second length and a second maximum outer diameter less than the first maximum outer diameter;
        a first marker section immediately and proximately adjacent the first reduced diameter section, the first marker section having a third length and a maximum outer diameter about equal to the first maximum outer diameter;
        a second reduced diameter section immediately and proximately adjacent the first marker section, the second reduced diameter section having the second length and the second maximum outer diameter;
        a second marker section immediately and proximately adjacent the second reduced diameter section, the second marker section having the third length and a maximum outer diameter about equal to the first maximum outer diameter; and
        a third reduced diameter section immediately and proximately adjacent the second marker section, the third reduced diameter section having a fourth length and the second maximum outer diameter, the fourth length less than or equal to the second length,
        wherein the third length is less than half the first length, and wherein the first marker section and the second marker section include a tapping thread similar to the continuous tapping section tapping thread.

2. The dense tissue tap apparatus of claim 1, wherein the continuous tapping section, the first marker section, and the second marker section are formed of a substantially radiopaque material.

3. The dense tissue tap apparatus of claim 1, wherein the elongated shaft is cannulated from its proximal end to its distal end along its longitudinal axis.

4. The dense tissue tap apparatus of claim 1, wherein the dense tissue tap apparatus is configured to create a threaded tap for a threaded implant having a maximum outer diameter greater than the first maximum outer diameter.

5. The dense tissue tap apparatus of claim 1, wherein the continuous tapping section, the first marker section, and the second marker section tapping threads include similar spiral threads.

6. The dense tissue tap apparatus of claim 5, wherein the continuous tapping section spiral thread is spirally aligned with the first marker section spiral thread and the second marker section spiral thread along the shaft.

7. The dense tissue tap apparatus of claim 6, wherein the dense tissue tap apparatus is configured to create a spiral threaded tap for a spiral threaded implant having a maximum outer diameter greater than the first maximum outer diameter.

8. The dense tissue tap apparatus of claim 7, wherein the dense tissue is bony tissue and the threaded implant is a bone screw.

9. The dense tissue tap apparatus of claim 6, wherein the first length is a first integer multiple of a first number and the sum of the second length and the third length is a second integer multiple of the first number, the second integer multiple less than the first integer multiple.

10. The dense tissue tap apparatus of claim 9, wherein the first number is 5 mm.

11. The dense tissue tap apparatus of claim 10, wherein the first integer multiple is 7 and the second integer multiple is 2.

12. The dense tissue tap apparatus of claim 1, the elongated shaft proximal end including a tool coupling interface.

13. The dense tissue tap apparatus of claim 1, wherein the third length is less than one tenth of the first length.

14. The dense tissue tap apparatus of claim 1, wherein the first length is a first integer multiple of a first number and the sum of the second length and the third length is a second integer multiple of the first number, the second integer multiple less than the first integer multiple.

15. The dense tissue tap apparatus of claim 14, wherein the first number is 5 mm.

16. The dense tissue tap apparatus of claim 15, wherein the first integer multiple is 7 and the second integer multiple is 2.

17. The dense tissue tap apparatus of claim 15, wherein the dense tissue is bony tissue and the dense tissue tap apparatus is configured to create a threaded tap for a threaded implant having a maximum outer diameter greater than the first maximum outer diameter.

18. The dense tissue tap apparatus of claim 15, wherein the third length is less than one tenth of the first length.

\* \* \* \* \*